United States Patent
Donati et al.

(10) Patent No.: US 6,379,695 B1
(45) Date of Patent: *Apr. 30, 2002

(54) BETAMETHASONE- AND HYALURONIC ACID-TREATED THIN ADHESIVE PLASTER FOR THE TREATMENT OF PSORIASIS DERMATITIS AND DERMATOSIS

(75) Inventors: Elisabetta Donati, Cavallasca (IT); Irina Rapaport, Rovio (CH)

(73) Assignee: Altergon S.A., Lugano (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/425,475

(22) Filed: Oct. 22, 1999

(30) Foreign Application Priority Data

Mar. 5, 1999 (IT) .......................... MI99A0449

(51) Int. Cl.$^7$ .................. A61F 13/02; A61F 13/00; A61L 15/16
(52) U.S. Cl. .................. 424/448; 424/449; 424/443
(58) Field of Search ................. 424/443, 449, 424/448

(56) References Cited

U.S. PATENT DOCUMENTS

| | | | |
|---|---|---|---|
| 4,990,340 A | * | 2/1991 | Hidaka et al. ............. 424/449 |
| 5,173,302 A | | 12/1992 | Holmblad et al. |
| 5,176,916 A | * | 1/1993 | Yamanaka et al. .......... 424/448 |
| 5,336,767 A | * | 8/1994 | Della Valle et al. ....... 536/55.1 |
| 5,773,028 A | * | 6/1998 | Inagi et al. |
| 5,891,920 A | * | 4/1999 | Hirano et al. ............... 514/625 |
| 5,932,227 A | * | 8/1999 | Higo et al. ................ 424/401 |
| 6,207,184 B1 | * | 3/2001 | Ikeda et al. |

FOREIGN PATENT DOCUMENTS

| | | | | |
|---|---|---|---|---|
| EP | 0 282 156 | | 9/1988 | |
| EP | WO 91/07974 | * | 6/1991 | ......... A61K/31/725 |
| EP | 0 965 626 | | 12/1999 | |

* cited by examiner

Primary Examiner—Thurman K. Page
Assistant Examiner—Isis Ghali
(74) Attorney, Agent, or Firm—Hedman & Costigan, P.C.

(57) ABSTRACT

Thin adhesive plaster having a thickness lower than 500 μm for the treatment of psoriasis, dermatitis and dermatosis, comprising:
a) a support comprising an outer layer in plastic film and an inner layer in woven or non-woven fabric having approximately the same size as the plastic film,
b) an adhesive layer placed on the support inner layer having approximately the same size as the support comprising an adhesive matrix in the form of hydrogel, betamethasone or a pharmaceutically acceptable salt thereof and optionally hyaluronic acid or a pharmaceutically acceptable salt thereof,
c) a protective plastic film contacted with the adhesive layer and removable immediately prior to use.

11 Claims, No Drawings

BETAMETHASONE- AND HYALURONIC ACID-TREATED THIN ADHESIVE PLASTER FOR THE TREATMENT OF PSORIASIS DERMATITIS AND DERMATOSIS

FIELD OF THE INVENTION

The present invention refers to a plaster in the form of a thin film for the treatment of slight psoriasis, allergic dermatitis, and dermatosis.

STATE OF THE ART

Corticosteroids are amply used in cases of eczema, dermatitis, contact dermatitis, psoriasis, etc., being remarkably efficacious for the treatment of skin diseases. However, prolonged treatments with said drugs cause untoward side effects at a systemic level, such as for example the suppression of the adrenocortical pituitary function, a phenomenon taking place even when corticosteroids are for external use and administered locally.

Further side effects arising from a prolonged administration of corticosteroids consist in skin infections, such as for example acne. That is the reason why the hormone is administered locally at very low concentrations.

However, a formulation containing corticosteroids in a low concentration to be administered locally does not secure a sufficient therapeutic effect on said diseases of the immune system. An approach to increase the corticosteroid percutaneous absorption consisted in the use of said active ingredient in a therapeutic formulation for local use containing a percutaneous absorption promoter, such as urea, propylene glycol, etc.

Another approach consisted in the use of a therapeutic tape exploiting the so-called occlusive dressing technique.

Therefore, the need for a therapeutic system for local use that does not cause ill effects and at the same time secures a remarkable therapeutic efficacy is deeply felt.

International patent application WO 91/07974 discloses a composition for local use containing a corticosteroid and hyaluronic acid. Thanks to the presence of hyaluronic acid, said composition has a decidedly lower corticosteroid content in respect of the compositions found in commerce. However, said composition has the typical drawbacks of the formulations for local use, i.e. the quantity of active ingredient to be applied to the skin area to be treated cannot be dosed precisely, and said application does not allow the active ingredient release at a controlled rate over a period of time.

SUMMARY OF THE INVENTION

It has surprisingly been found that it is possible to make up for the cons of the prior art by using the adhesive plaster of the present invention, which contains corticosteroid in a very low quantity and, at the same time, allows an accurate control of the corticosteroid dosage which may be released at a controlled rate on the skin area to be treated.

In particular, said adhesive plaster characterized by having a very low thickness, lower than 500 μm, comprises:
  a) a support comprising an outer layer in plastic film and an inner layer in woven or non-woven fabric having approximately the same size as the plastic film,
  b) an adhesive layer placed on the support inner layer having approximately the same size as the support comprising an adhesive matrix in the form of hydrogel, betamethasone or a pharmaceutically acceptable salt thereof and optionally hyaluronic acid or a pharmaceutically acceptable salt thereof,
  c) a protective plastic film contacted with the adhesive layer and removable immediately prior to use.

DETAILED DESCRIPTION OF THE INVENTION

The adhesive plaster according to the present invention preferably contains both active ingredients in the adhesive layer.

Betamethasone is present in the adhesive plaster according to the present invention as betamethasone valerate; the hyaluronic acid preferably has a molecular weight ranging from 30,000 to 1,200,000, and more preferably from 30,000 to 300,000, and is preferably present as sodium salt. The adhesive plaster being the object of the present invention is generally 200 to 500 μm thick and preferably 250 to 480 μm thick.

The support outer layer is a film made of a polymeric material preferably selected from a group comprising polyethylene, ethylene-methyl methacrylate copolymer, polypropylene; the support inner layer is made of woven or non-woven fabric, preferably selected from the group comprising polyethylene, polypropylene, rayon. Adhesive layer (b) contains an adhesive hydrogel matrix comprising polyacrylic acid in an aqueous dispersion, with a polyacrylic acid concentration ranging from 0.1 to 9% by weight in respect of the adhesive layer total weight.

According to a preferred embodiment, the aqueous dispersion used is as found in commerce under the trademark AC10H®; its viscosity ranges from 10,000 to 50,000 mPa.s. and its polyacrylic acid content is in a concentration of 20% by weight.

The aforesaid aqueous dispersion is added in concentrations ranging from 10 to 30% by weight, and preferably in a concentration of 20% by weight, in respect of the adhesive layer total weight.

The adhesive plaster adhesive layer preferably weighs 150 to 400 m$^2$/g and is 120 to 280 μm thick.

According to a preferred embodiment, the adhesive layer contains betamethasone valerate in a concentration of 0.05 to 5% by weight, and more preferably of 0.1% by weight in respect of the adhesive layer total weight, and sodium hyaluronate in a concentration of 0.1% to 3% by weight and still more preferably of 0.2% by weight in respect of the adhesive layer total weight.

The adhesive layer may contain excipients selected from preservatives, wetting agents, thickeners, cross-linking agents, pH adjusters, stabilisers, etc., and mixtures thereof.

The thickeners preferably used are sodium polyacrylate having a molecular weight of 450,000 to 4,000,000, polyacrylic acid having a molecular weight of 450,000 to 4,000,000, sodium carboxymethylcellulose or mixtures of said thickeners. The preservatives preferably used are methylparaben, propylparaben, and more preferably mixtures of the said preservatives. The cross-linking agent is preferably dihydroxyaluminium amino acetate. The wetting agent is preferably selected from the group comprising glycerol, butylene glycol, propylene glycol or mixtures thereof. The stabiliser is preferably sodium edetate; the pH adjuster is preferably tartaric acid.

The adhesive plaster according to the present invention is prepared on the basis of the following method. The hydrocolloidal matrix is co-extruded between the support film and the protective plastic film to be removed immediately prior to use. The preparation of the adhesive plaster according to the invention is reported in the following examples, conveyed by way of indication.

EXAMPLE 1A

Preparation of the Support Layer

The adhesive matrix was prepared by mixing the components in a turbomixer and co-extruded between the two layers (support and protective layers). The sandwich obtained was cut to the desired size, so that the adhesive layer of each adhesive plaster would contain the components shown in the following table

| Components | % by weight | Mg/adhesive plaster |
|---|---|---|
| Betamethasone valerate | 0.1 | 1.5 |
| Sodium hyaluronate | — | — |
| Methylparaben | 0.1 | 1.5 |
| Propylparaben | 0.05 | 0.75 |
| Butylene glycol | 3.00 | 45.00 |
| Glycerol | 39.00 | 585.00 |
| Polyacrylic acid | 1.0 | 15.00 |
| 20% Polyacrylic acid aqueous dispersion | 20.00 | 300.00 |
| Sodium polyacrylate | 4.00 | 60.00 |
| Sodium carboxymethylcellulose | 4.60 | 69.00 |
| Hydroxypropyl methylcellulose | 0.50 | 7.50 |
| Dihydroxyaluminium amino acetate | 0.06 | 0.90 |
| Disodium edetate | 0.07 | 1.05 |
| Tartaric acid | 1.50 | 22.50 |
| Water | Balance to 100 | 390.30 | or as reported in the following table:

| Components | % by weight | mg/adhesive plaster |
|---|---|---|
| Betamethasone valerate | 0.1 | 1.5 |
| Sodium hyaluronate | 0.2 | 3.0 |
| Methylparaben | 0.1 | 1.5 |
| Propylparaben | 0.05 | 0.75 |
| Butylene glycol | 3.00 | 45.00 |
| Glycerol | 39.00 | 585.00 |
| Polyacrylic acid | 1.00 | 15.00 |
| 20% polyacrylic acid aqueous dispersion | 20.00 | 300.00 |
| Sodium polyacrylate | 4.00 | 60.00 |
| Sodium carboxy methylcellulose | 4.60 | 69.00 |
| Hydroxypropyl methylcellulose | 0.50 | 7.50 |
| Dihydroxyaluminium amino acetate | 0.06 | 0.90 |
| Disodium edetate | 0.07 | 1.05 |
| Tartaric acid | 1.50 | 22.50 |
| Water | balance to 100 | 387.30 |

EXAMPLE 1B

Adhesive Layer Application to the Support Material

The aforesaid composition was applied to the support weighing 225 mg and 75 μm thick by co-extrusion to obtain an adhesive plaster 280 μm thick and weighing, without the removable film, 1.5 g.

EXAMPLE 1C

The protective polyethylene terephthalate film 75 μm thick was applied.

What is claimed is:

1. An adhesive plaster having a thickness lower than 500 μm consisting of:

a) a support consisting of an outer layer in plastic film and an inner layer in woven or non-woven fabric having approximately the same size as the plastic film, (b) an adhesive layer placed on the support inner layer approximately the same size as the support, said layer consisting essentially of an adhesive matrix in the form of hydrogel, betamethasone valerate, sodium hyaluronate, a thickener, a preservative, a wetting agent, a cross-linking agent, a stabilizer and a pH adjuster, and (c) a protective plastic film contacted with the adhesive layer and removable immediately prior to use wherein the concentration of betamethasone valerate in the adhesive layer is 0.1% by weight and the concentration of sodium hyaluronate in the adhesive layer is 0.2% by weight.

2. The adhesive plaster as claimed in claim 1, wherein the sodium hyaluronate has a molecular weight ranging from 30,000 to 1,200,000.

3. The adhesive plaster as claimed in claim 1, wherein the adhesive plaster thickness ranges from 200 to 500 μm.

4. The adhesive plaster as claimed in claim 1, wherein the adhesive plaster thickness ranges from 250 to 480 μm.

5. The adhesive plaster as claimed in claim 1, wherein the support layer is made of woven or non-woven fabric, selected from the group consisting of polyethylene, polypropylene and polypropylene.

6. The adhesive plaster as claimed in claim 1, wherein the support inner layer is made of woven or non-woven fabric, selected from the group consisting of polyethylene, polypropylene and rayon.

7. The adhesive plaster as claimed in claim 1, wherein the thickeners contained in the adhesive layer are selected from the group consisting of sodium polyacrylate having a molecular weight of 450,000 to 4,000,000, polyacrylic acid having a molecular weight of 450,000 to 4,000,000, sodium corboxymethylcellulose and mixtures thereof.

8. The adhesive plaster as claimed in claim 1, wherein the preservatives contained are selected from the group consisting of methylparaben, propylparaben, and mixtures thereof.

9. The adhesive plaster as claimed in claim 1, wherein the wetting agent is selected from the group consisting of glycerol, butylene glycol, propylene glycol and mixtures thereof.

10. The adhesive plaster as claimed in claim 1, wherein the cross-linking agent contained in the adhesive layer is dihydroxyaluminium amino acetate.

11. The adhesive plaster as claimed in claim 1, wherein the stabiliser is sodium edetate and the pH adjuster is tartaric acid.

\* \* \* \* \*